(12) United States Patent
Salerni

(10) Patent No.: US 7,749,232 B2
(45) Date of Patent: Jul. 6, 2010

(54) ELECTROMAGNETICALLY GUIDED SPINAL ROD SYSTEM AND RELATED METHODS

(76) Inventor: Anthony Salerni, 17 Veronica Dr., Bedford, NH (US) 03110

( * ) Notice: Subject to any disclaimer, the term of this patent is extended or adjusted under 35 U.S.C. 154(b) by 1179 days.

(21) Appl. No.: 11/306,673

(22) Filed: Jan. 6, 2006

(65) Prior Publication Data

US 2006/0276803 A1  Dec. 7, 2006

Related U.S. Application Data

(60) Provisional application No. 60/683,943, filed on May 24, 2005.

(51) Int. Cl.
*A61B 17/58* (2006.01)
(52) U.S. Cl. .......... 606/103; 606/914; 606/99; 606/250; 606/264; 600/424
(58) Field of Classification Search .......... 606/103, 606/99, 86 A, 86 R, 250, 251, 252, 253, 254, 606/255, 256, 257, 258, 259, 260, 261, 262, 606/263, 264, 265, 266, 267, 268, 269, 270, 606/271, 272, 273, 274, 275, 276, 277, 278, 606/279, 86 S, 914, 915, 916, 86 B, 104; 600/429, 426, 423, 424
See application file for complete search history.

(56) References Cited

U.S. PATENT DOCUMENTS

| 5,513,637 | A | * | 5/1996 | Twiss et al. ............. 600/424 |
| 6,340,363 | B1 | | 1/2002 | Bolger et al. |
| 6,348,058 | B1 | | 2/2002 | Melkent et al. |
| 6,530,929 | B1 | * | 3/2003 | Justis et al. ............. 606/103 |
| 6,796,988 | B2 | | 9/2004 | Melkent et al. |
| 7,160,300 | B2 | * | 1/2007 | Jackson ............. 606/273 |
| 7,250,052 | B2 | * | 7/2007 | Landry et al. ............ 606/86 A |
| 7,473,267 | B2 | * | 1/2009 | Nguyen et al. ............. 606/279 |
| 7,520,879 | B2 | * | 4/2009 | Justis et al. ............. 606/86 A |
| 7,527,638 | B2 | * | 5/2009 | Anderson et al. ......... 606/279 |
| 7,588,588 | B2 | * | 9/2009 | Spitler et al. ............ 606/246 |
| 2003/0114752 | A1 | * | 6/2003 | Henderson et al. ......... 600/433 |
| 2004/0015215 | A1 | | 1/2004 | Fredricks et al. |
| 2004/0030395 | A1 | | 2/2004 | Blunn et al. |
| 2004/0102824 | A1 | | 5/2004 | Sharkey et al. |
| 2004/0152970 | A1 | | 8/2004 | Hunter et al. |
| 2004/0171924 | A1 | | 9/2004 | Mire et al. |

(Continued)

FOREIGN PATENT DOCUMENTS

| EP | 1 037 567 B1 | 10/2004 |
| EP | 1 504 726 A1 | 2/2005 |
| EP | 1 523 950 A1 | 4/2005 |

*Primary Examiner*—Eduardo C Robert
*Assistant Examiner*—Jan Christopher Merene
(74) *Attorney, Agent, or Firm*—Robert R. Deleault, Esq.; Mesmer & Deleault, PLLC

(57) ABSTRACT

An electronically guided spinal rod system for the placement of a spinal rod into the heads of pedicle screws and other types of bone fixation systems includes a bone screw inserter having rod access slots extending longitudinally for a length along the screw inserter, a rod detection system coupled to the rod access slots and a rod pusher for inserting a spinal rod through the rod access slots. The electronically guided spinal rod system insures that the spinal rod will be accurately positioned while allowing the operator complete freedom to choose its specific path into the screw inserter rod access slots.

16 Claims, 6 Drawing Sheets

U.S. PATENT DOCUMENTS

| | | |
|---|---|---|
| 2004/0199072 A1 | 10/2004 | Sprouse et al. |
| 2005/0043742 A1* | 2/2005 | Bruneau et al. .............. 606/99 |
| 2005/0059885 A1 | 3/2005 | Melkent et al. |
| 2005/0065517 A1* | 3/2005 | Chin .......................... 606/61 |
| 2005/0070917 A1* | 3/2005 | Justis ........................ 606/104 |
| 2005/0085714 A1 | 4/2005 | Foley et al. |
| 2005/0154389 A1* | 7/2005 | Selover et al. ................ 606/61 |
| 2005/0192570 A1* | 9/2005 | Jackson ...................... 606/61 |
| 2005/0192589 A1* | 9/2005 | Raymond et al. ............. 606/99 |
| 2005/0251139 A1* | 11/2005 | Roh ............................ 606/61 |
| 2005/0277934 A1* | 12/2005 | Vardiman .................... 606/61 |
| 2009/0062858 A1* | 3/2009 | Dziedzic et al. ............ 606/278 |

* cited by examiner

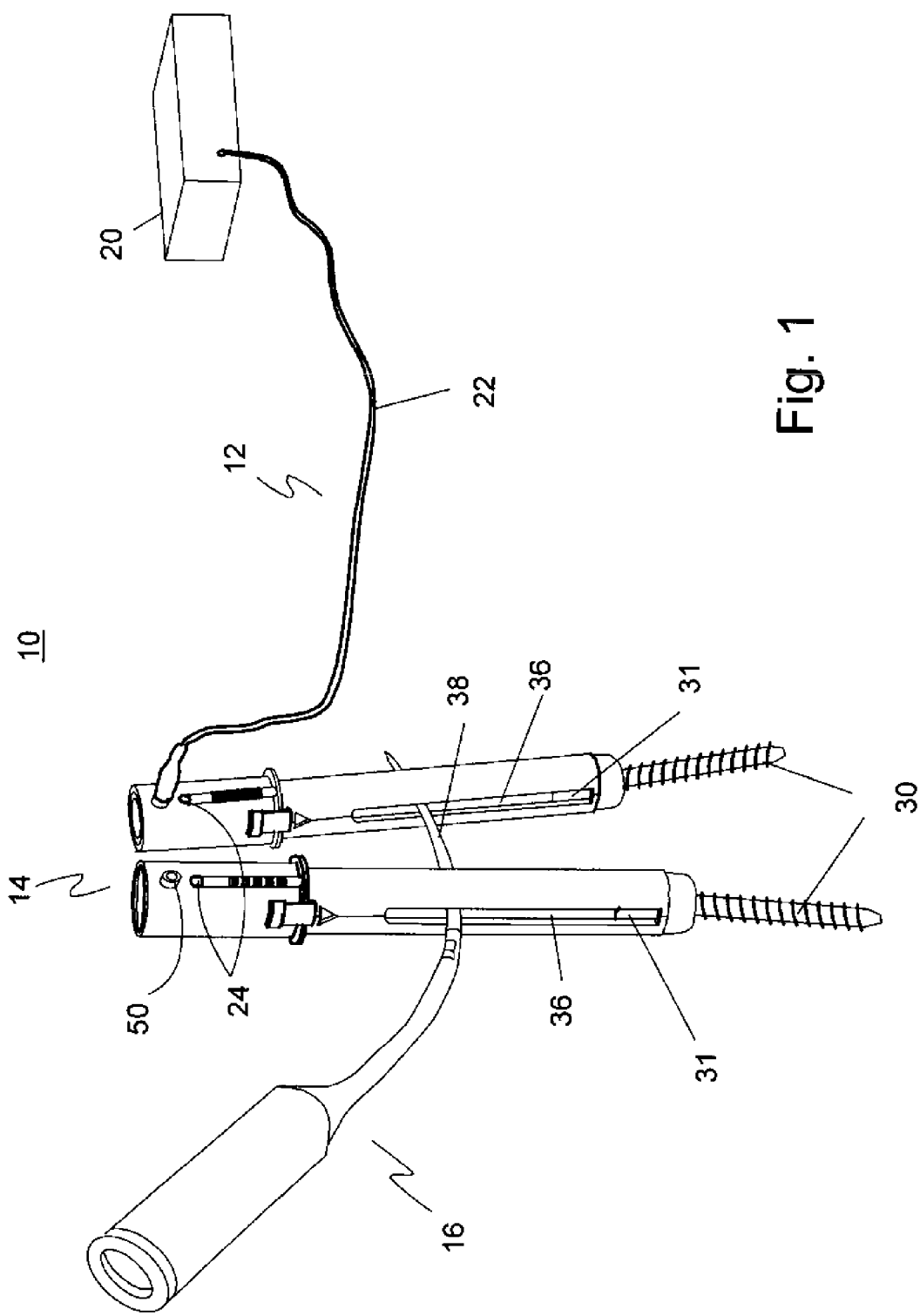

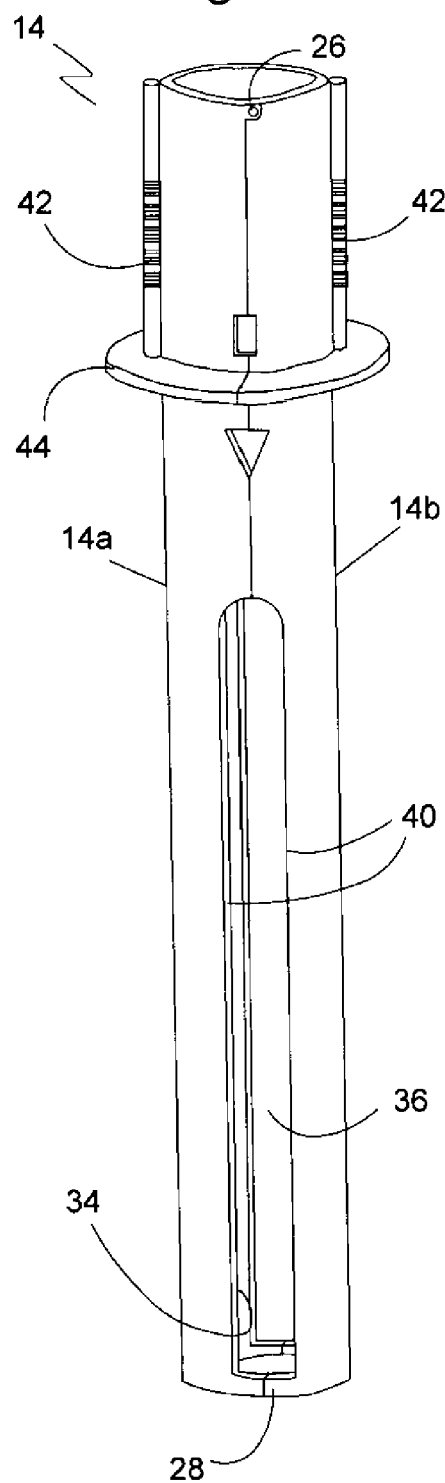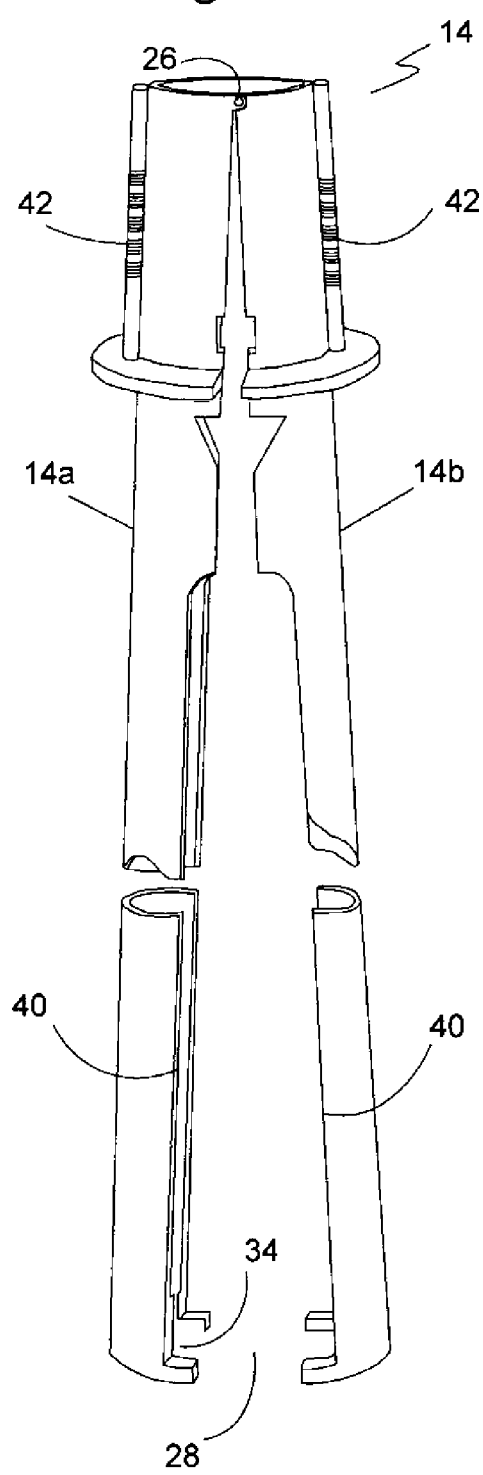

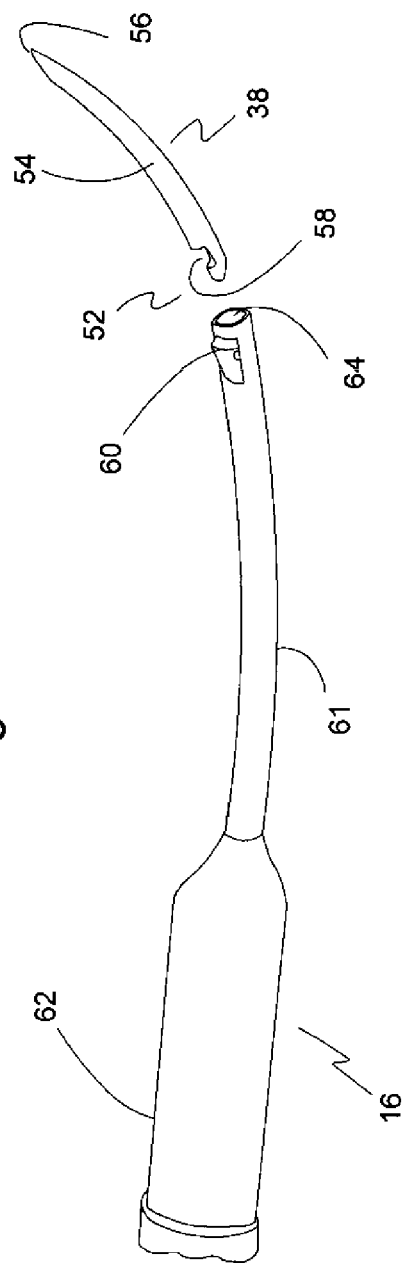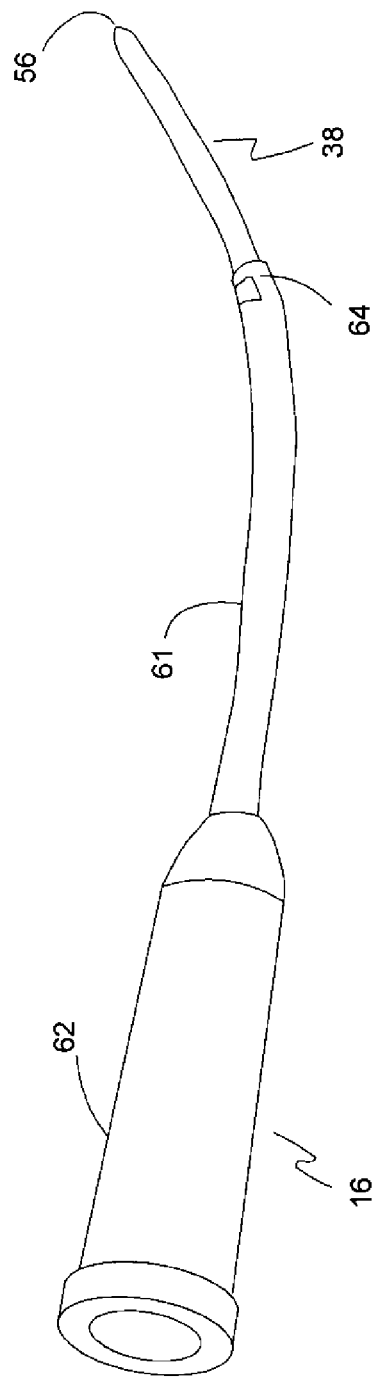

ELECTROMAGNETICALLY GUIDED SPINAL ROD SYSTEM AND RELATED METHODS

This application claims the benefit of U.S. Provisional Patent Application No. 60/683,943, filed May 24, 2005.

BACKGROUND OF THE INVENTION

I. Field of the Invention

The present invention relates generally to spinal surgery and, more particularly, to an electromagnetically guided spinal rod system for the placement of pedicle screws, rods and other types of bone fixation systems.

II. Discussion of the Prior Art

It can be appreciated that bone screw/rod fixation systems have been in use for years. Typically, bone screw/rod fixation systems designed for spinal surgery are comprised of a number of pedicle screws and rods having a main purpose to secure one or more spinal segments. This technique is used to stabilize the spine across the vertebral levels to which it is applied in order to augment the fusion process. To be operational, most systems require one or more rods to be placed inside openings in the heads of bone screws that have been pre-positioned in the vertebrae. Most fixation systems are positioned after an extensive surgical dissection has stripped the musculature completely off the posterior aspects of the vertebrae involved. After placement of the screws, the rods are inserted via the open operating window. A less common method involves a percutaneous approach such as the one disclosed in U.S. Pat. No. 6,530,929 to Justis et al., in which the rods are passed through a narrow incision (such as, by way of example only, a stab wound) after the pedicle screws have been placed. In this type of system the rod is guided into the screw heads by a mechanical arm attached to the screw inserters.

The main problem with conventional bone screw/rod fixation systems is that the extensive muscular dissections required by the open (as opposed to percutaneous) pedicle screw and rod systems produce potentially severe adverse clinical effects. While there are some newer methods designed to reduce the tissue damage accompanying pedicle screw and rod insertion, most spinal fixation systems require the potentially disabling extensive dissection of the surrounding muscular tissue. One problem associated with conventional percutaneous bone screw/rod fixation systems is that the insertion step is done blindly. Accurate rod placement is completely dependent upon the proper functioning of the mechanical arm that controls the rod and its geometric relationship to the various screw heads.

In the existing percutaneous spinal fixation systems, there are no built-in mechanisms that indicate how closely the rods actually follow their intended paths or more importantly, whether or not the rods reach their proper resting position between the screw heads and the gaps in the screw inserters. Another problem with current percutaneous bone screw/rod fixation systems is that the trajectory or path that the rod takes to its target is completely determined by the geometric parameters of the rod positioning system. Specifically, once the procedure has begun, the operating physician cannot modify the rod insertion trajectory. Due to variations in the anatomical structure of different patients and the particular angles of the screw placements, the capacity to modify the path of the rod once the procedure has begun is a very desirable feature. Furthermore, the reliance of existing percutaneous systems on a "one-path" method of rod placement make such systems extremely sensitive to the position of the pedicle screws if more than two screws per side are used, reducing the available trajectories for pedicle screw placement.

While these devices may be adequate for the particular purpose to which they are addressed, they do not provide the least invasive means possible for the placement of pedicle screws, rods and other types of bone fixation systems. The present invention cures this deficiency by the application of a novel concept governing positioning of the rod.

SUMMARY OF THE INVENTION

The present invention accomplishes this goal by providing an electromagnetically guided spinal rod system that insures that the rod will be accurately positioned while allowing the operator complete freedom to choose its specific path.

To attain this, the present invention generally comprises mechanisms that allow the operator to accurately position a rod through channels in the heads of bone screws via a percutaneous route. According to one broad aspect of the present invention, the electromagnetically guided spinal rod system comprises an electrified rod detection system, a screw inserter, and a rod pusher. The rod detection system may consist of a pair of antennae and an electronic detector circuitry that processes signals picked up by the antennae in each inserter. The antennae are located within the walls of the screw inserters, preferably along the opposing edges of the rod access slots, which are formed by cut-away regions running longitudinally for a substantial length of the screw inserter. The electronic detection circuitry may be self-contained and is connected to each antenna by a data transmitting cable. Each antenna/detection circuit pair power proximity LEDs that illuminate when the rod is in close proximity to the specific LED's respective antenna.

The screw inserters may be tubular structures having a generally cylindrical cross-section. In a preferred embodiment, the screw inserters may be longitudinally sectioned and hingedly attached at a proximal end. This hinged relationship allows the molded screw head receiver at the distal end of the screw inserter to be opened so that it may accept a pedicle screw head. When the screw head receiver is closed, the screw inserter may be secured to the screw head by engaging a screw inserter hinge lock. Cut-away regions in each opposing edge of the lower half of the screw inserters may serve as rod access slots. The rod access slots are slightly bigger than the spinal rod, which is to pass through the slots. The edges of the rod access slots comprise the rod detection area. The antennae imbedded in the walls of the inserter along the edges of this area are in electrical continuity with the signal relay junctions located on the sides of the upper third of each longitudinal half of the screw inserter.

The screw inserter hinge lock is a tubular structure having a generally cylindrical cross-section and an inner diameter generally equivalent to the outer diameter of the portion of the screw inserter located proximally of the hinge lock plate. A hinge lock plate may serve as a stop that provides the lowest position that the screw inserter hinge lock can occupy. The screw inserter hinge lock may be secured to the hinge lock plate by a pair of hinge lock clips. The screw inserter hinge lock includes a pair of signal relay junction channels comprised of generally tubular protrusions dimensioned to snugly fit over the signal relay junctions on the screw inserter. The signal relay junction channels may be fitted with electrical contacts to communicate with the signal relay junctions. The proximal end of each signal relay junction channel may be fitted with a proximity LED. The electrical contacts imbedded in the signal relay junction channels are also in electrical continuity with the hinge lock data port. Thus, the hinge lock data port is in electrical continuity to each of the proximity LEDs.

The spinal rod is approximately 5 mm in diameter, tapered at its leading end and uniformly curved. It is designed to fit into the rod access slots in each screw inserter. The rod pusher is a wand-like device that has a handle at one end and a receiver for the trailing end of the rod at the other. The handle permits the operator to manipulate the rod, which is attached to the receiver along the desired path.

A primary object of the present invention is to provide an electromagnetically guided spinal rod system that will overcome the shortcomings of the prior art devices.

It is an object of the present invention to provide an electromagnetically guided spinal rod system for the placement of a rod through the head of pedicle screws and other types of bone fixation systems by the least invasive means possible. The rod passing guidance system of the present invention insures that the rod will be accurately positioned while allowing the operator complete freedom to choose its specific path.

Another object of the present invention is to provide an electromagnetically guided spinal rod system that will allow a surgeon to place pedicle screws and rods through percutaneous stab incisions, thus eliminating extensive muscular dissections and other adverse clinical conditions.

Another object of the present invention is to provide a electromagnetically guided spinal rod system that makes the choice of position for pedicle screw placement independent of the rod passing mechanism characteristic of other percutaneous pedicle screw systems.

Another object of the present invention is to provide an electromagnetically guided spinal rod system that allows the operator freedom to choose the most appropriate path for placement of the percutaneous rod.

Another object of the present invention is to provide an electromagnetically guided spinal rod system that can furnish the operator with information concerning the spatial relationship between the rod and the screw inserters so that the operator may accurately guide the rod into its proper position.

Other objects and advantages of the present invention will become obvious to the reader and it is intended and contemplated that these objects and advantages are within the scope of the present invention.

To the accomplishment of the above and related objects, this invention may be embodied in the form illustrated in the accompanying drawings, with attention being called to the fact, however, that the drawings are illustrative only and that changes may be made in the specific construction illustrated. In that respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways.

BRIEF DESCRIPTION OF THE DRAWINGS

Many advantages of the present invention will be apparent to those skilled in the art with a reading of this specification in conjunction with the attached drawings, wherein like reference numerals are applied to like elements.

FIG. 1 is a perspective view of one embodiment of an electromagnetically guided spinal rod system of the present invention.

FIGS. 2A & 2B are perspective views of a closed and opened screw inserter according to one embodiment of an electromagnetically guided spinal rod system of the present invention.

FIG. 6A is a perspective view of a rod-pusher and rod according to one embodiment of the present invention.

FIG. 6B is a perspective view of the rod-pusher and rod of FIG. 6A coupled together in preparation for use.

DESCRIPTION OF THE PREFERRED EMBODIMENT

Figure 3:
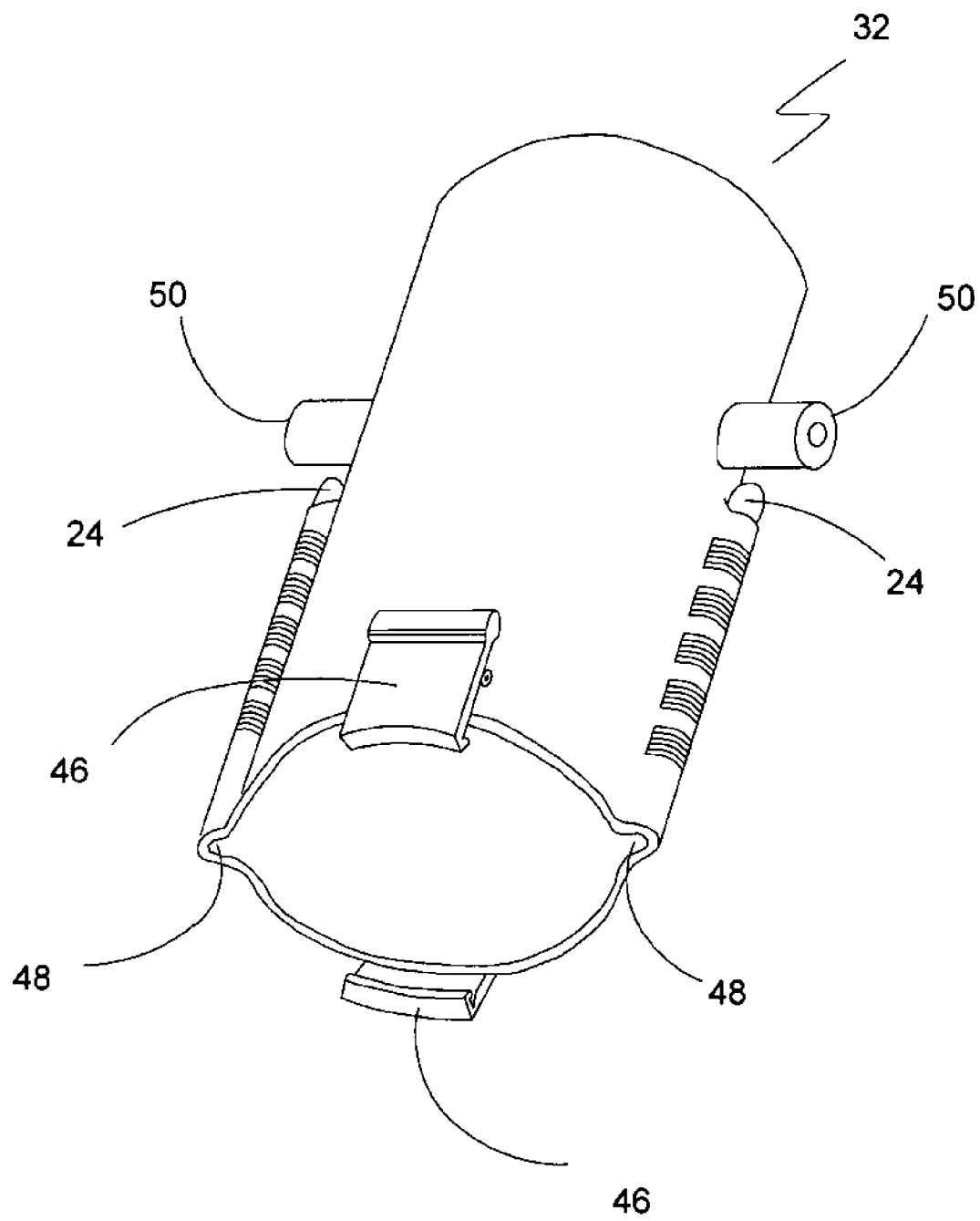
FIG. 3 is a perspective view of a screw inserter hinge lock according to one embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The electromagnetically guided spinal rod system and related methods disclosed herein boasts a variety of inventive features and components that warrant patent protection, both individually and in combination.

FIG. 1 illustrates an electromagnetically guided spinal rod system 10 of the present invention. The electromagnetically guided spinal rod system 10 includes at least one each of an electronic rod detection system 12, a screw inserter 14, and a rod pusher 16. The electronic rod detection system 12 is composed of two antennae 18 (best viewed in FIG. 5) and an electronic detection circuitry 20 that processes the signals detected by antennae 18 and transmitted via a data transmitting cable 22. The antennae 18 may be located within the walls of the screw inserter 14, preferably in close proximity to the opposing edges of rod access slots 36. The electronic detection circuitry 20 may be self-contained and connected to each antenna 18 by a data transmitting cable 22 through a data port 50. Each pair of antennae 18 and detection circuit 20 may be configured to power a proximity light-emitting diode (LED) 24 that illuminates when the rod 38 is in close proximity to the specific LEDs 24 respective antenna 18.

Figure 4:
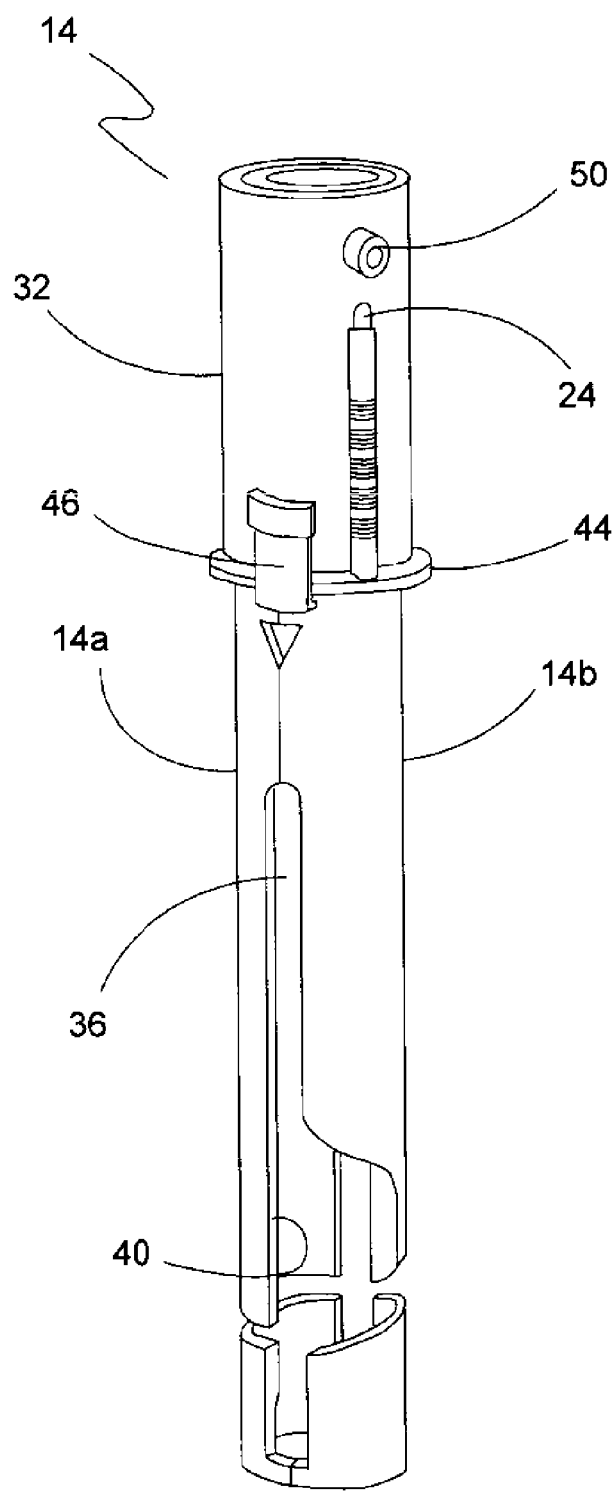
FIG. 4 is a rotated perspective view of the screw inserter of FIG. 2A mated with a screw inserter hinge lock according to one embodiment of the present invention.

FIGS. 2A & 2B illustrate a preferred embodiment of a screw inserter 14 according to the present invention. The screw inserter 14 is a longitudinally sectioned tubular structure having a generally cylindrical cross-section. The longitudinal sectioning of the screw inserter 14 effectively divides the inserter 14 into two halves, 14a, 14b, which are joined together at the proximal end by a hinge 26. This hinged coupling allows the molded screw head receiver 28 to be opened so that it may accept the head 31 of a pedicle screw 30. When the screw head receiver 28 is closed, the screw inserter 14 may be secured to the pedicle screw head 31 by engaging the screw inserter hinge lock 32 (FIGS. 3 & 4). Recesses 34 cut into the opposing edges of screw inserter halves 14a, 14b form a rod access slot 36 when the screw inserter 14 is in a closed position. The rod access slot 36 is slightly wider than the diameter of the rod 38, which is to pass through it. Due to the preferred proximate location of the rod access slot 36, the edges of the rod access slot 36 may function as a rod detection area 40. The antennae 18 imbedded in the walls of the inserter 14 along the edge of the recess 34 are in electrical continuity with the signal relay junctions 42, located on the sides of the proximal portion of each screw inserter half 14*a*, 14*b*. A hinge lock plate 44 serves as a stop providing the lowest position that the screw inserter hinge lock 32 can occupy. Optionally, the molded screw head receiver 28 may be fashioned with teeth or protuberances that mate with depressions or slots in the bone screw head 31 that may be designed to be used with the electromagnetically guided spinal rod system 10 of the present invention.

FIGS. 3 & 4 illustrate a preferred embodiment of a screw inserter hinge lock 32 according to the present invention. The screw inserter hinge lock 32 is an elongated tubular structure having a generally cylindrical cross-section and an inner diameter generally equivalent to the outer diameter of the portion of the screw inserter 14 located proximally of the hinge lock plate 44. The hinge lock 32 is secured to the hinge lock plate 44 by a pair of hinge lock clips 46. The screw inserter hinge lock 32 includes a pair of signal relay junction channels 48 comprised of generally tubular protrusions dimensioned to snugly fit over the signal relay junctions 42 on the screw inserter 14. The signal relay junction channels 48 may be fitted with electrical contacts to communicate with the signal relay junctions 42. The proximal end of each signal relay junction channel 48 may be fitted with a proximity LED 24. The electrical contacts imbedded in the signal relay junction channels 48 are also in electrical continuity with the hinge lock data port 50. Thus, the hinge lock data port 50 is in electrical continuity to each of the proximity LEDs 24.

Figure 5:
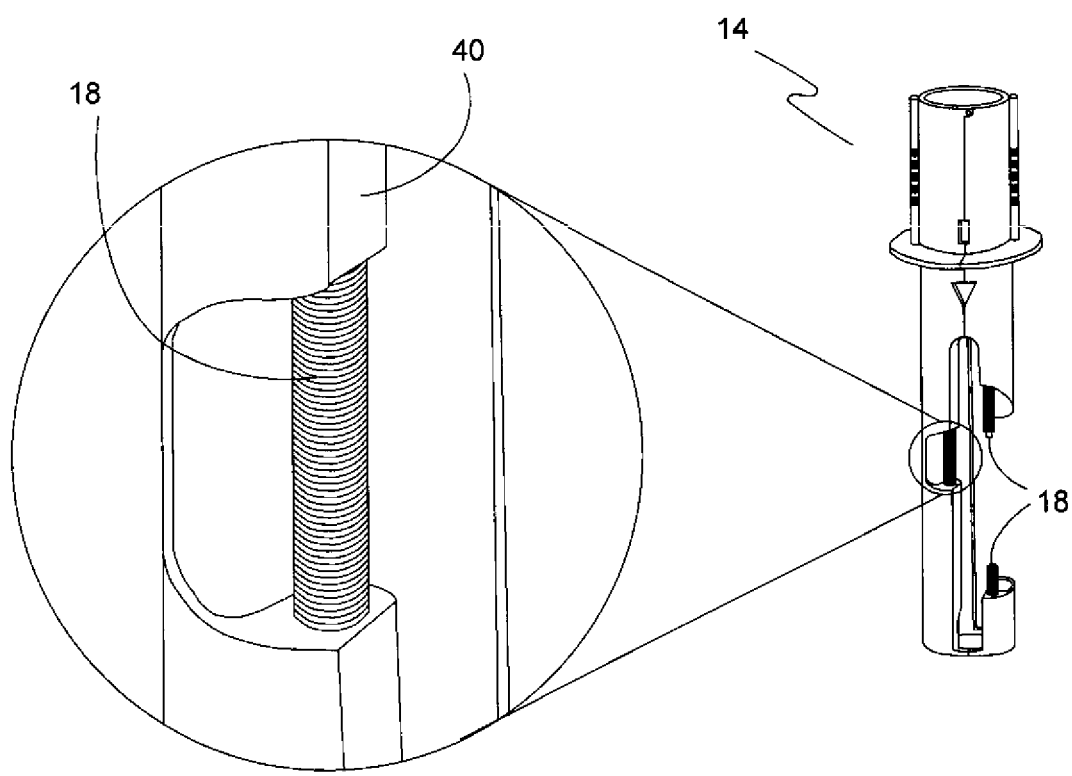
FIG. 5 is a cut-away view of the rod detection area of a screw inserter according to one embodiment of the present invention particularly illustrating, in a magnified view, an internal antenna.

FIG. 5 provides a cutout view of a screw inserter 14 of the present invention, showing a preferred location of antennae 18. The rod detection system 12 is composed of two antennae 18 located within the walls of the screw inserters 14 (preferably along opposing edges of the rod access slots 36) and a electronic detection circuitry 20 comprised of at least two identical electronic detection circuits that process signals transmitted from antennae 18 by way of data transmitting cable 22. The circuitry 20 may be designed to detect the presence of a rod 38, which by way of example only, may be generally metallic in composition. A proximity LED 24 associated with each antenna 18/detection circuit 20 pair may illuminate upon detection of rod 38 as the rod approaches and/or passes the rod detection area 40. Each respective LED 24 may be located at the proximal ends of the signal relay junction channels 48 on the screw inserter hinge lock 32, and will be driven by the detection circuitry 20 that is connected to the antenna 18 on its respective side.

FIGS. 6A & 6B illustrate a rod pusher 16 and spinal rod 38 according to one embodiment of the present invention. Spinal rod 38 includes a proximal end 52, a shaft 54, and a distal end 56. By way of example only, the rod 36 may be approximately 5 mm in diameter, tapered at its distal (leading) end 56 and uniformly curved along shaft 54. The rod 38 is designed to fit into the rod access slots 36 in each screw inserter 14. The rod 38 may be composed of any material suitable for use in to the human body. The proximal (trailing) end 52 may include a lock slot 58 that engages a rod gripping mechanism 60 in the rod pusher 16. It may be advantageous in some instances for the rod 38 to be hollow. In such a case, the distal end 56 may be fitted with a signal-generating antenna if the detection circuitry 20 required it. The signal may be transmitted to this antenna by means of a cable running the length of the hollow rod 38. In this case the cable would terminate in contacts that protrude from the proximal end 52 and communicate with contacts in the rod pusher 16. The rod pusher 16 may contain a signal generating power source. In such an embodiment, the rod 38 would itself be electrified, emitting a signal that would then be detected by rod detecting area 40 and transmitted to the LEDs 24. Thus, the surgeon would then be able to detect the presence, and therefore the accurate placement of spinal rod 38.

The rod pusher 16 is a wand-like device having a handle 62 at the proximal end and a receiver 64 at the distal end dimensioned to receive the proximal end 52 of the rod 38. The handle 62 is used to drive the rod 38 through human tissue to the rod access slots 36, permitting the operator to manipulate the rod 38 along a desired trajectory. The rod gripping mechanism 60 is positioned at the distal end of rod pusher 16, in close proximity to the receiver 64. The receiver 64 is recessed or hollowed to the dimensions that allow the proximal end 52 of the rod 38 to precisely fit into it. The rod gripping mechanism 60 consists of a slide lock that, when moved towards the handle 62 by an actuator, will engage the lock slot 58 on the proximal end 52 of the rod 38, thereby securing the rod 38 to the rod pusher 16. The handle 62 and shaft 61 of the rod pusher 16 may be hollow to permit the passage of the components of the slide lock actuator and any electrical cables that are required by the specific detection circuitry 20 used. In the event that it is considered advantageous to fit the rod 38 with a signal generator or other electronic device the hollow in the shaft 61 and handle 62 of the rod pusher 16 will be used as a conduit to allow transit of any necessary data transmission cables. It is expected that these cables will terminate in an electronic receptacle or data/power port in the handle 62.

In use, the first step required for the operation of the preferred embodiment of the electromagnetically guided spinal rod system 10 according to the present invention is to fit each screw inserter 14 with a bone screw 30. To accomplish this, the screw inserter 14 is moved to the "open" position (as shown in FIG. 2B), separating the distal ends of the screw inserter halves 14*a*, 14*b* by swinging them about the screw inserter hinge 26. The head 31 of a bone screw 30 is then mated to the screw head receiver 28 located at the distal end of the open screw inserter 14. The screw inserter 14 is then "closed" about the screw heads 31 by swinging the screw inserter halves 14*a*, 14*b* about the screw inserter hinge 26 in a direction opposite to that which was required to move screw inserter 14 into the "open" position. The screw inserter 14 is then secured to the bone screw 30 by sliding a screw inserter hinge lock 32 over each screw inserter 14. Once the bone screw 30 is secured to the screw inserter 14, it is surgically placed into the appropriate vertebrae using standard surgical techniques. This process may be repeated with multiple sets of screw inserters 14 and bone screws 30 depending on the number of bone screws 30 required by the particular surgical procedure. By way of example only, FIG. 1 depicts an electromagnetically guided spinal rod system 10 used to implant a pair of bone screws 30. However, it is contemplated that any number of bone screws 30, and therefore bone screw inserters 14, may be used.

After screw placement, the data transmission cable 22 from the rod detection circuitry is connected to the hinge lock data port 50 on each of the screw inserters 14. The proximal end 52 of the spinal rod 38 is locked to the distal end of the rod pusher 16. A mechanical switch on the handle 62 is activated that engages the rod gripping mechanism 60 against the rod 38, thereby securing the rod 38 to the rod pusher 16. Once in this position, the rod 38 in effect becomes an extension of the handle 62 of the rod pusher 16 and thus it may be manipulated in space by the operator's control of the handle 62. The distal end 56 of the spinal rod 38 is inserted through the skin at a distance from the skin entry point of the target screw inserter 14. Using a combination of visual cues provided by the position of this screw inserter 14 and fluoroscopic imaging, the distal end 56 of the rod 38 is placed in proximity to the target rod access slot 36 of a first rod inserter 14 by the force applied to the handle 62 of the rod pusher 16 by the operator. Once inside a threshold radius from the antennae 18 in the rod access slots 36, the rod detection circuitry 20 senses the presence of the rod 38.

In the event that the trajectory of the rod 38 carries it along the plane defined by the rod access slots 36, both proximity LEDs 24 on the first rod inserter 14 will illuminate confirming the fact that the rod 38 is being inserted along the correct trajectory. If the trajectory of the rod 38 takes it to the side of the first screw inserter 14, the path will carry the rod 38 closer to one antenna 18 than the other. In this case the rod detection circuitry 20 will illuminate the proximity LED 24 on the side of the rod access slot 36 that is closer to the path of the rod 38. The operator then uses this information to correct the trajectory of the rod 38. The operator may repeatedly alter the path of the rod on the basis of the information provided by the proximity LEDs 24 until both proximity LEDs 24 remain illuminated while lateral fluoroscopic images show that the rod 38 has passed completely through the rod access slot 36 of the first screw inserter 14. By the application of force through the rod pusher handle 62, the operator continues to advance the rod 38 along this trajectory until it passes the threshold radius of the antennae 18 associated with a second screw inserter 14. The rod 38 is guided through the rod access slot 36 of the second screw inserter 14 by the information provided by its proximity LEDs 24. This process is repeated until the rod 38 has been passed through the rod access slots 36 in each of the screw inserters 14.

Once the rod 38 is accurately inserted, a rod gripper (not shown) may be inserted into one of the screw inserters 14 and advanced distally along its longitudinal axis until the gripper engages the rod 38. The rod gripping mechanism 60 is deactivated and the rod pusher 16 is disengaged from the rod 38 and removed from the patient. The rod 38 is subsequently forced into the screw heads 31 that are secured to the molded screw head receivers 28 located at the distal ends of the screw inserters 14. Once the rod 38 is satisfactorily positioned in each of the screw heads 31, the locking mechanism specific to the screw that secures the rod 38 to the screw 30 is activated (not shown). After the rod 38 is secured to each of the screw heads 31 in this manner, the screw inserter hinge lock 32 is removed from each screw inserter 14 and then each screw inserter 14 is pried open and removed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. By way of example only, it is anticipated that alternative means to secure the screw heads to the screw inserters could be developed that would make a hingedly coupled longitudinally sectioned tubular inserter unnecessary. In such a case, the screw inserter 14 could be comprised of a single generally cylindrical member equipped with an alternative means to secure the bone screw to the inserter.

The rod detection system 12 is designed for the purpose of providing information to the operator concerning the spatial relationship between the rod 38 and the rod access slots 36. It is conceivable that in some instances this information may be better supplied if the signal detection apparatus is placed in the rod 38 for the purpose of detecting the rod access slot 36 or screw heads 31. The detection system 12 as described is a passive system designed specifically for a typical generally metallic rod 38. It is anticipated that an alternative embodiment may include active detections systems in which the detector may be designed to detect and respond to radio frequency as well as other types of electromagnetic and acoustical energy. With detector configurations such as these it is understood that a signal generator emitting the energy specific to the particular detector may be built into the leading end of the rod 38. Furthermore, it is also anticipated that it may be useful to modulate, digitize or in some manner electronically manipulate this signal for the purpose of enhancing the spatial information that is being sought.

What is claimed is:

1. An electromagnetically guided spinal rod system for placing a spinal rod into screw heads of screws positioned in bone material, said spinal rod system comprising:
   an elongated, tubular-shaped screw inserter having a top portion with signal relay junctions located on opposite sides of said top portion and rod access slots extending longitudinally for a length along said screw inserter;
   a screw inserter hinge lock having signal relay junction couplings wherein said inserter hinge lock has a structure for disposing over said top portion and wherein said signal relay junction couplings are electrically coupled to said signal relay junctions located on opposite sides of said top portion
   a rod detection system adjacent to said rod access slots of said screw inserter and electrically coupled to said signal relay junctions;
   and a rod pusher having a handle and a curved portion with a spinal rod receiver wherein said curved portion is sized to guide the spinal rod into said rod access slots.

2. The spinal rod system of claim 1 further comprising an electronic detection circuitry coupled to said rod detection system.

3. The spinal rod system of claim 1 wherein said top portion has a stop.

4. The spinal rod system of claim 1 wherein said screw inserted has a first longitudinal half, a second longitudinal half and a hinge between said first longitudinal half and said second longitudinal half.

5. The spinal rod system of claim 1 wherein said top portion includes an LED light coupled to each of said signal relay junctions.

6. The spinal rod system of claim 1 wherein said screw inserter hinge lock includes a proximity LED light coupled to each of said signal relay junction couplings.

7. The spinal rod system of claim 1 wherein said rod detection system includes antennae.

8. The spinal rod system of claim 1 wherein said screw inserter hinge lock includes a hinge lock clip.

9. The spinal rod system of claim 1 wherein said screw inserter hinge lock includes a hinge lock data port.

10. The spinal rod system of claim 1 wherein said spinal rod receiver of said rod pusher includes a spinal rod gripping mechanism for removable engagement of the spinal rod.

11. The spinal rod system of claim 10 wherein said spinal rod gripping mechanism includes a slide lock.

12. The spinal rod system of claim 1 wherein said rod pusher includes a signal generator circuitry.

13. A method of electronically guiding a spinal rod into a screw head of a bone screw, said method comprising:
   inserting, through the skin of a patient at a distance from the skin entry point of a tubular-shaped screw inserter having a pair of rod access slots, a distal end of a spinal rod that is secured to a spinal rod pusher;
   wherein said tubular-shaped screw inserter has a top portion with signal relay junctions located on opposite sides of said top portion, a screw inserter hinge lock disposed over said top portion, said screw inserter hinge lock having signal relay couplings that are electrically coupled to said signal relay junctions located on opposite sides of said top portion,
   positioning the spinal rod using visual cues provided by electronic signals generated by the placement of the spinal rod through said pair of rod access slots of said screw inserter, said screw inserter having a rod detection system coupled to said rod access slots; and
   disengaging said spinal rod pusher from the spinal rod after said spinal rod is positioned within said rod access slots and after a rod gripper engages the spinal rod through said screw inserter.

14. A method for making a guiding system to electronically position a spinal rod into proper alignment with a screw head of a bone screw, said method comprising:
   providing a pair of rod access slots that extend longitudinally along a bone screw inserter below a screw inserter top portion;
   coupling a rod detection system to said pair of rod access slots;
   electrically coupling said rod detection system to a pair of signal junctions of said top portion, wherein a screw inserter hinge lock having signal relay junction couplings is disposed over said top portion and wherein said signal relay couplings are electrically coupled to said signal relay junctions located on opposite sides of said top portion,
   providing a rod pusher having a handle and a curved portion with a receiver for detachably receiving a spinal rod, said rod pusher being independent of said screw inserter but structured for positioning the spinal rod through said pair of rod access slots; and
   providing electronic detection circuitry coupled to said rod detection system.

15. The method of claim 14 wherein said rod detection system coupling step further includes embedding antennae within the walls of said rod access slots.

16. The method of claim 14 further comprising including signal generating circuitry in said rod pusher.

* * * * *